(12) United States Patent
Sornes (10) Patent No.: US 9,888,178 B2
(45) Date of Patent: Feb. 6, 2018

(54) METHOD AND SYSTEM FOR ENHANCED STRUCTURAL VISUALIZATION BY TEMPORAL COMPOUNDING OF SPECKLE TRACKED 3D ULTRASOUND DATA

(71) Applicant: General Electric Company, Schenectady, NY (US)

(72) Inventor: Anders R. Sornes, Oslo (NO)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 693 days.

(21) Appl. No.: 14/074,969

(22) Filed: Nov. 8, 2013

(65) Prior Publication Data

US 2015/0130901 A1 May 14, 2015

(51) Int. Cl.
| | |
|---|---|
| *H04N 13/02* | (2006.01) |
| *H04N 5/232* | (2006.01) |
| *G01S 15/89* | (2006.01) |
| *G01S 7/52* | (2006.01) |
| *A61B 8/08* | (2006.01) |
| *G06T 7/246* | (2017.01) |

(52) U.S. Cl.
CPC ....... *H04N 5/23267* (2013.01); *A61B 8/0833* (2013.01); *A61B 8/483* (2013.01); *A61B 8/5246* (2013.01); *G01S 7/52077* (2013.01); *G01S 15/8925* (2013.01); *G01S 15/8993* (2013.01); *G06T 7/246* (2017.01); *G01S 15/8913* (2013.01); *G01S 15/8995* (2013.01); *G06T 2207/10132* (2013.01); *G06T 2207/30004* (2013.01)

(58) Field of Classification Search
CPC ................................ A61B 8/08; G06T 7/0012
USPC ............................................ 348/46; 600/443
See application file for complete search history.

(56) References Cited

U.S. PATENT DOCUMENTS

2010/0249592 A1* 9/2010 Langeland ............... A61B 8/08
600/443

OTHER PUBLICATIONS

"A Motion Compounding Technique for Speckle Reduction in Ultrasound Images," Cheng-Hsien Lin, Yung-Nien Sun, Chii-Jeng Lin, http://www.ncbi.nlm.nih.gov/pmc/articles/PMC3046654.

(Continued)

*Primary Examiner* — Jamie Atala
*Assistant Examiner* — Masum Billah
(74) *Attorney, Agent, or Firm* — McAndrews, Held & Malloy, Ltd.; Jacob Groethe; David Bates (57) ABSTRACT

An ultrasound device acquires ultrasound image data corresponding to a plurality of volume frames of an object and applies morphing or motion compensation to the acquired ultrasound image data to track a particular region of the object. The ultrasound device compounds the motion compensated ultrasound image data that corresponds to the tracked particular region of the object within the plurality of volume frames of the object. The ultrasound device generates a stationary single three dimensional (3D) volume of the tracked particular region of the object. The ultrasound device acquires the ultrasound image data over at least a portion of a movement cycle. The ultrasound device generates motion tracking information and speckle tracking information from the acquired ultrasound image data for the tracked particular region of the object and group pixels corresponding to the tracked particular region of the object based on the generated motion tracking and speckle tracking information.

20 Claims, 4 Drawing Sheets

(56) References Cited

OTHER PUBLICATIONS

"Motion Compounding for Ultrasound Image Sequences," http://vision.csie.ncku.edu.tw/~linjs/USCompound/.
"Temporal Enhancement of 3D Echocardiography by Frame Reordering," Douglas P. Perrin, PhD, Nikolay V. Vasilyev, MD, Gerald R. Marx, MD and Pedro J. del Nido, MD, JACC Cardiovascular Imaging © 2012 by The American College of Cardiology Foundation, vol. 5, No. 3, 2012, pp. 300-304.

* cited by examiner

METHOD AND SYSTEM FOR ENHANCED STRUCTURAL VISUALIZATION BY TEMPORAL COMPOUNDING OF SPECKLE TRACKED 3D ULTRASOUND DATA

CROSS-REFERENCE TO RELATED APPLICATIONS/INCORPORATION BY REFERENCE

This application makes reference to:
U.S. application Ser. No. 13/179,212, which was filed on Jul. 18, 2011, and which is entitled "Method and Apparatus for Performing Ultrasound Elevation Compounding;" and
U.S. Pat. No. 8,224,053, which was issued on Aug. 1, 2013, and which is entitled "Method and System for Displaying Quantitative Segmental Data in 4D Rendering."

Each of the above referenced patent and patent publication is hereby incorporated herein by reference in its entirety.

FIELD OF THE INVENTION

Certain embodiments of the invention relate to ultrasound imaging. More specifically, certain embodiments of the invention relate to a method and system for enhanced structural visualization by temporal compounding of speckle tracked 3D ultrasound data.

BACKGROUND OF THE INVENTION

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

In ultrasound imaging, speckle noise occurs as a result of interference of scattered echo signals reflected from an object, such as an organ. The speckle noise or speckle appears as a granular grayscale pattern on an image. The speckle noise degrades image quality and increases the difficulty of discriminating fine details in images during diagnostic examinations. Speckle noise may degrade image quality since the speckles obtained from different angles are incoherent, Some ultrasound systems are capable of spatially compounding a plurality of ultrasound images of a given target into a compound image. The term "compounding" generally refers to non-coherently combining multiple data sets to create a new single data set. The plurality of data sets may each be obtained from imaging the object from different angles, using different imaging properties, such as, for example, aperture and/or frequency, and/or imaging nearby objects (such as slightly out of the plane steering). These compounding techniques may be used independently or in combination to reduce speckle and improve image quality.

In conventional ultrasound imaging, the image is acquired by a series of scan lines. This results in an image in which some anatomical structures may be "shadowed" by objects closer to the transducer whose stronger reflections have drained the beam energy along that scan line. This may be referred to as shadowing. Moreover, dense diagonal structures may not be optimally imaged as they will tend to reflect energy in other directions than back to the transducer. Typically, when the boundaries of anatomical structures are parallel to the ultrasonic transducer, the acoustic waves reflect directly back to the ultrasonic transducer with less dispersion and a clear image is obtained. However, diagonal or vertical structures are sub-optimally imaged using conventional ultrasound because of the lower percentage of acoustic energy that reflects back to the ultrasonic transducer. Furthermore, structures that are hidden beneath strong reflectors are also sub-optimally imaged.

A plurality of data sets or compound frames imaging the same target but under different conditions may be combined to generate a single view or compound image by combining the data received from each point in the compound image target that has been received from each compound frame. An ultrasonic transducer array may be utilized to implement the difference in the conditions under which the individual component data is acquired by means of electronic beam steering and/or electronic translation of the component frames. The component frames are combined into a compound image by summation, averaging, peak detection, or other combinational means. The compounded image may display reduced speckle pattern and enhanced specular reflector delineation than a non-compounded ultrasound image, which serves to emphasize structural information in the image.

Visualizing anatomical features of organs such as anomalies in the heart walls, and in particular the coronary apparatus, may be occluded by the fact that a given frame of ultrasound data insonifies an anatomical region from only one particular angle since the degree of backscattering may be very angle dependent, as are effects like shadowing and reverberation from surrounding structures and deflection of energy from the inclination of the structure itself, all effects that contribute to masking such features out. The image quality of such features could also suffer from a poor signal/noise ratio or low contrast to the surroundings. They may be difficult to visually identify because of their changing location and appearance from frame to frame because of the heart motion. Moreover the resolution needed to see such structures could be compromised by high frame rate demands generally posed in 3D cardiac imaging in order to capture the heart dynamics.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for enhanced structural visualization by temporal compounding of speckle tracked 3D ultrasound data, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Certain embodiments of the invention may be found in a method and system for enhanced structural visualization by temporal compounding of speckle tracked 3D ultrasound data.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

In addition, as used herein, the phrase "pixel" also includes embodiments of the present invention where the data is represented by a "voxel". Thus, both the terms "pixel" and "voxel" may be used interchangeably throughout this document.

Also as used herein, the phrase "reconstructing an image" is not intended to exclude embodiments of the present invention in which data representing an image is generated, but a viewable image is not generated. Therefore, as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
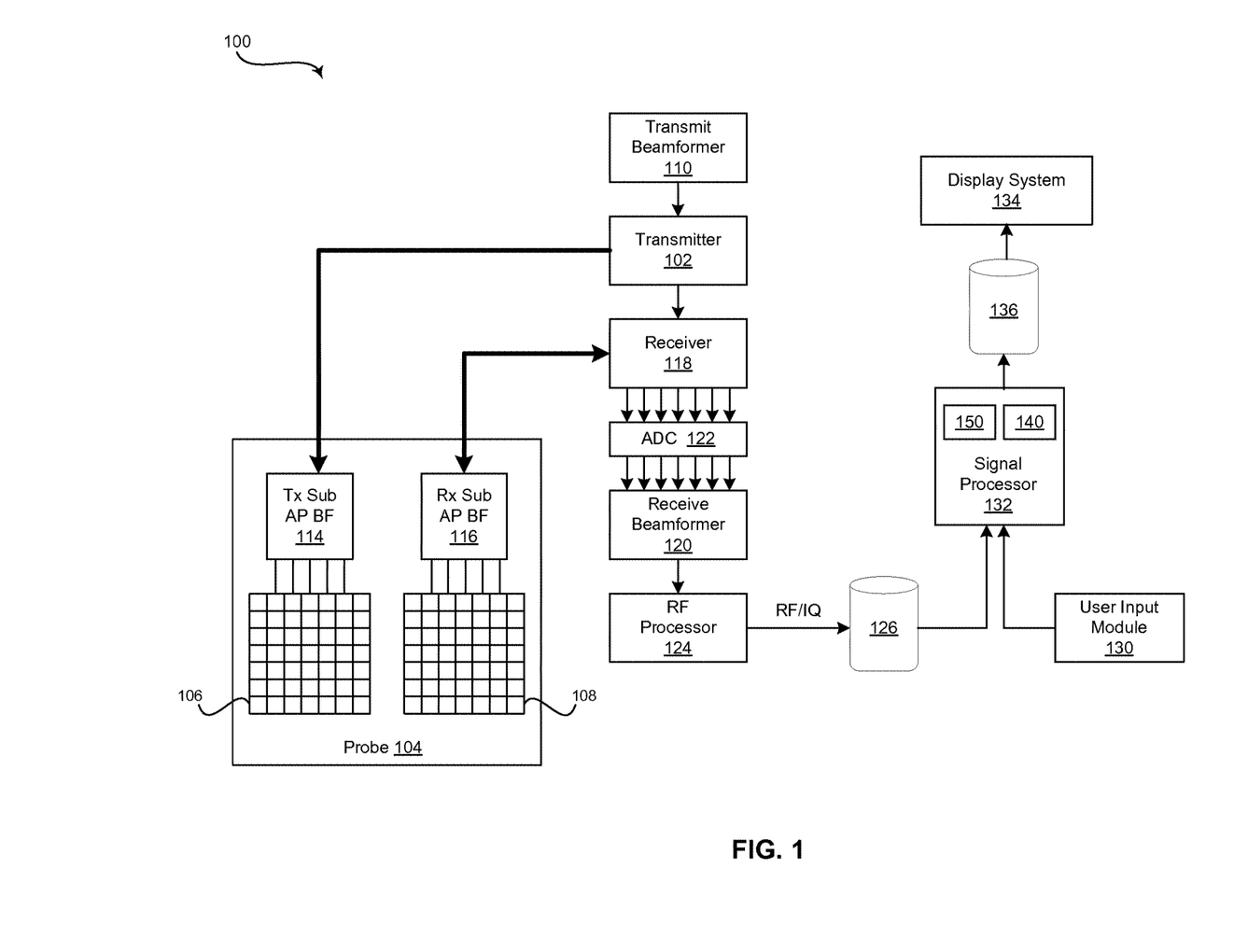
FIG. 1 is a block diagram of an exemplary ultrasound system that is operable to provide enhanced structural visualization by temporal compounding of speckle tracked 3D ultrasound data, in accordance with an embodiment of the invention.

FIG. 1 is a block diagram of an exemplary ultrasound system that is operable to provide enhanced structural visualization by temporal compounding of speckle tracked 3D, in accordance with an embodiment of the invention. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130 a signal processor 132, an image buffer 136, a display system 134, a spatial compounding module 140 and a processing module 150.

The transmitter 102 may comprise suitable logic, circuitry, interfaces and/or code that may be operable to drive an ultrasound probe 104.

The ultrasound probe 104 may comprise suitable logic, circuitry, interfaces and/or code, which may be operable to perform some degree of beam steering, which may be perpendicular to the scan plane direction. The ultrasound probe 104 may comprise a 3D array. In an exemplary embodiment of the invention, the ultrasound probe 104 may comprise a three dimensional (3D) array of elements that is operable to steer a beam in the desired spatial 3D direction. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells, to produce echoes which return to the group of receive transducer elements 108. The echoes are received by the receive transducer elements 108 and may include undesirable speckle (e.g., interference caused by scattered echo signals reflected from the region of interest).

The group of receive transducer elements 108 in the ultrasound probe 104 may be operable to convert the received echoes into analog signals, undergo sub-aperture beamforming by a receive sub-aperture beamformer 116 and are then communicated to a receiver 118.

The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated with in the receiver 118.

The receive beamformer 120 may comprise suitable logic, circuitry, interfaces and/or code that may be operable to perform digital beamforming processing on the signals received from the plurality of A/D converters 122. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126.

The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, scan parameters, settings, configuration, parameters, change scan mode, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, and/or the display system 134

The signal processor 132 may comprise suitable logic, circuitry, interfaces and/or code that may be operable to process the acquired ultrasound information (i.e., RF signal data or IQ data pairs) for presentation on a display system 134. The signal processor 132 is operable to perform one or more processing operations according to a plurality of selectable ultrasound modalities on the acquired ultrasound information. In en exemplary embodiment of the invention, the signal processor 132 may be operable to perform compounding, motion tracking, and/or speckle tracking. Acquired ultrasound information may be processed in real-time during a scanning session as the echo signals are received. Additionally or alternatively, the ultrasound information may be stored temporarily in the RF/IQ buffer 126 during a scanning session and processed in less than real-time in a live or off-line operation. In the exemplary embodiment, the signal processor 132 may comprise a spatial compounding module 140.

The ultrasound system 100 may be operable to continuously acquire ultrasound information at a frame rate that is suitable for the imaging situation in question. Typical frame rates range from 20-70 but may be lower or higher. The acquired ultrasound information may be displayed on the display system 134 at a display-rate that can be the same as the frame rate, or slower or faster. An image buffer 136 is included for storing processed frames of acquired ultrasound information that are not scheduled to be displayed immediately. Preferably, the image buffer 136 is of sufficient capacity to store at least several seconds worth of frames of ultrasound information. The frames of ultrasound information are stored in a manner to facilitate retrieval thereof according to its order or time of acquisition. The image buffer 136 may be embodied as any known data storage medium.

The spatial compounding module 140 is optional and may comprise suitable logic, circuitry, interfaces and/or code that may be operable to combine a plurality of steering frames corresponding to a plurality of different angles to produce a compound image. The spatial compounding module 140 may be operable to control the steering of the ultrasound signals generated by the plurality of transmit transducer elements 106 and/or the plurality of receive transducer elements 108 to a plurality of different angles. The spatial compounding module 140 may also be operable to control the steering of the ultrasound signals generated by the plurality of transmit transducer elements 106 and/or the plurality of receive transducer elements 108 to a plurality of angles.

Additional details on compounding may be found in U.S. application Ser. No. 13/179,212, which was filed on Jul. 18, 2011, and which is entitled "Method and Apparatus for Performing Ultrasound Elevation Compounding."

Additional details on motion compensation may be found in U.S. Pat. No. 8,224,053, which was issued on Aug. 1, 2013, and which is entitled "Method and System for Displaying Quantitative Segmental Data in 4D Rendering."

The processing module 150 may comprise suitable logic, circuitry, interfaces and/or code that may be operable to handle processing of ultrasound image data to provide enhanced structural visualization by temporal compounding of speckle tracked 3D ultrasound data. In this regard, the processing module 150 may generate tracking information, for example, motion tracking and speckle tracking information, for particular regions throughout the entirety of an object based on the captured and recorded 3D ultrasound image data. The processing module 150 may be operable to reorganize and/or transform the 3D ultrasound image data so that pixels corresponding to the same tracked particular region of the object in each of the plurality of captured frames or volume frames are grouped together, based on the generated tracking information. The processing module 150 may be operable to compound the plurality of captured frames in the image of the object by combining the pixels corresponding to the same tracked particular region of the object in each of the plurality of captured frames, which have been grouped together by, for example, averaging, median filtering, taking maximum and minimum values, etc.

In accordance with an embodiment of the invention, the ultrasound system 100 may be operable to record 3D ultrasound data of the heart over one or several heart cycles or a fraction of a heart cycle and generate motion tracking information such as speckle tracking for regions of the heart walls from the ultrasound data. The ultrasound system 100 may be operable to reorganize and/or transform the ultrasound data so that pixels corresponding to the same tracked tissue location in a plurality of captured frames of the image may be grouped together. The ultrasound system 100 may be operable to combine the corresponding frames for the same tracked tissue location into one single frame by compounding the pixel from the same tissue-stationary point from all the different frames together, for instance by averaging, median filtering, taking maximum or minimum values, etc. The resulting stationary single 3D frame may be presented or displayed either directly as a map in relation to a tissue stationary grid, or may be back transformed onto the original heart shape in a chosen phase of the heart cycle, for instance the diastole. This corresponding dataset from the compounding may be sliced, rendered or subjected to any type of 3D visualization scheme.

In an exemplary embodiment of the disclosure, the ultrasound system 100 may be operable to acquire ultrasound image data for a plurality of volume frames of the heart. The ultrasound system 100 may be operable to generate motion tracking information and/or the speckle tracking information from the acquired ultrasound image data. The ultrasound system 100 may be operable to apply motion compensation to the acquired ultrasound image data to track, or align between frames, a particular structure within the plurality of volume frames of the heart. The motion compensated ultrasound image data that corresponds to the tracked particular structure of the heart within the plurality of volume frames of the heart may be compounded and a stationary single 3D volume of the tracked particular structure in the heart may be generated. Some or all of the plurality of volume frames of the heart may be replaced by the compounded static frame morphed back onto the shape of the heart in the particular phase of the heart cycle that volume comes from in order to be able to visually track the particular structure in the heart. The ultrasound system 100 may be operable to perform the morphing based on motion the tracking information and/or the speckle tracking information, which is generated from the acquired ultrasound image data. The ultrasound system 100 may be operable to perform similar operations on objects or organs other than a heart.

The ultrasound system 100 is operable to provide high quality three dimensional visualization of the anatomical features of the heart, which may be stationary to the heart walls, such as the coronary apparatus, anomalies, and/or other features. In this regard, the ultrasound system may enable three dimensional assessment and diagnosing of the coronary anatomy as well as issues and anomalies.

Figure 2:
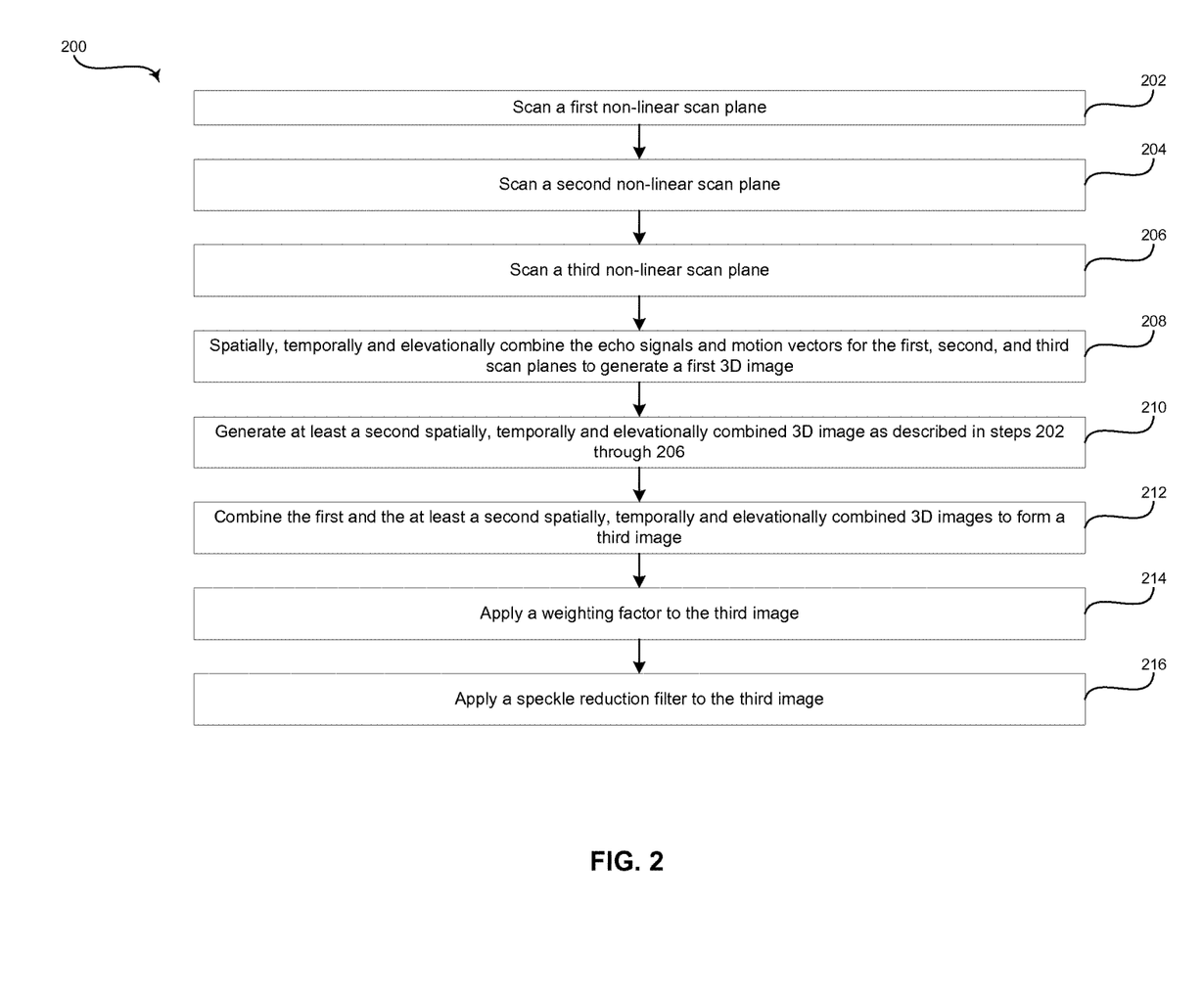
FIG. 2 is a flow chart illustrating exemplary steps that may be utilized for spatial image compounding, in accordance with an embodiment of the invention.

FIG. 2 is a flow chart illustrating exemplary steps that may be utilized for spatial image compounding, in accordance with an embodiment of the invention. Referring to FIG. 2, there is shown a flow chart 200 comprising exemplary steps 202 through 216. Spatial compounding is an imaging technique in which a number of echo signals from a number of adjacent imaging planes are combined. The multiple directions help achieve speckle de-correlation.

In step 202, the ultrasound probe 104 in the ultrasound system 100 may be operable to scan a first non-colinear scan plane.

In step 204, the ultrasound probe 104 in the ultrasound system 100 may be operable to scan a second non-colinear scan plane.

In step 206, the ultrasound probe 104 in the ultrasound system 100 may be operable to scan a third non-colinear scan plane. The user input module 130 may be operable to configure and/or control operation of the ultrasound probe 104 to scan the first, second, third and fourth non-linear scan planes.

In step 208, the signal processor 132 in the ultrasound system 100 may be operable to spatially, temporally and elevationally combine the echo signals and motion vectors for the first, second, and third scan planes to generate a first 3D image.

In step 210, the signal processor 132 in the ultrasound system 100 may be operable to generate at least a second spatially, temporally and elevationally combined 3D image as described in steps 202 through 206.

In step 212, the signal processor 132 in the ultrasound system 100 may be operable to combine the first and the at least a second spatially, temporally and elevationally combined 3D images to form a third image.

In step 214, the signal processor 132 in the ultrasound system 100 may be operable to apply a weighting factor to the third image.

In step 216, the signal processor 132 in the ultrasound system 100 may be operable to apply a speckle reduction filter to the third image.

Figure 3:
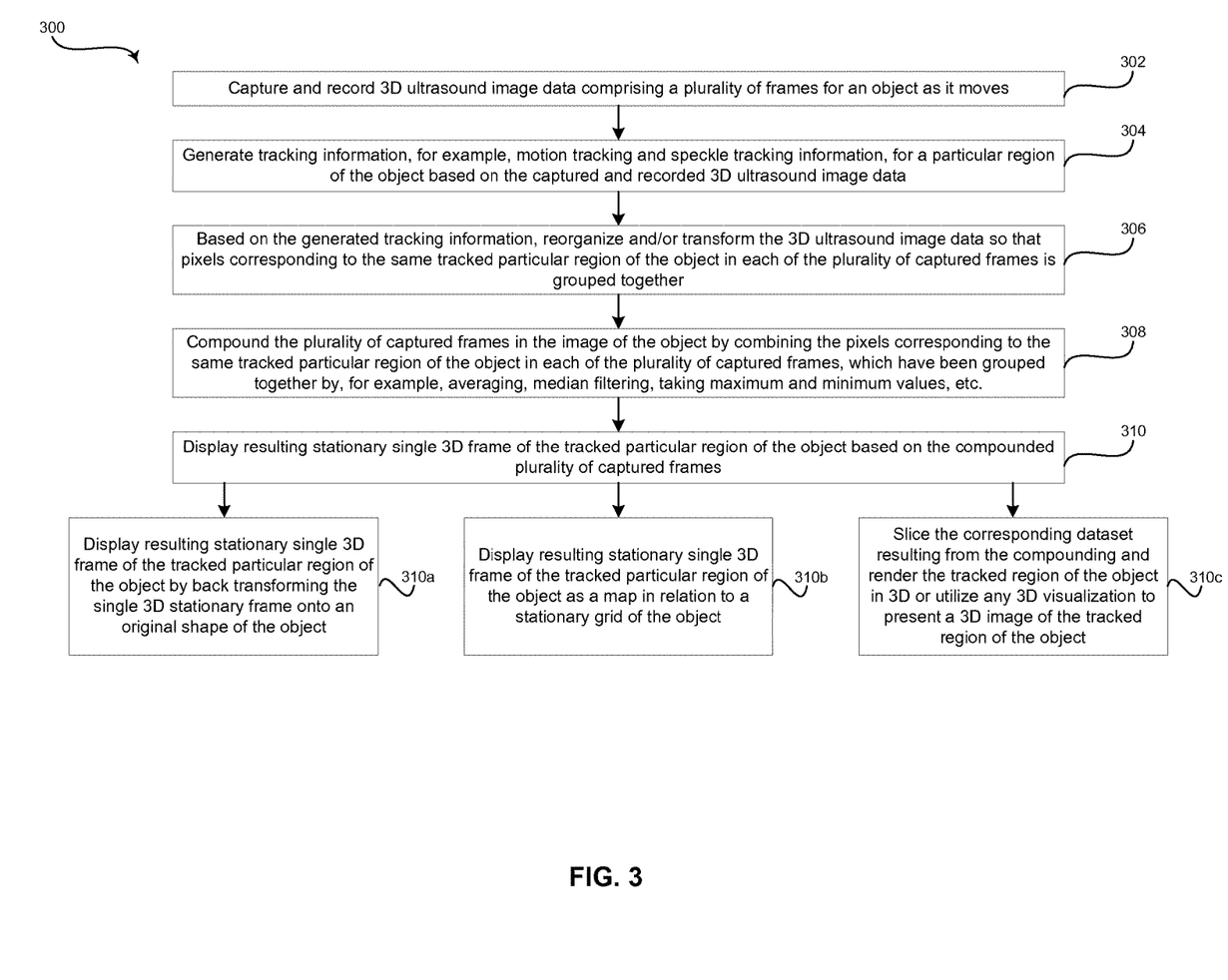
FIG. 3 is a flow chart illustrating exemplary steps for providing enhanced structural visualization by temporal compounding of speckle tracked 3D ultrasound data for a moving object, in accordance with an embodiment of the invention.

FIG. 3 is a flow chart illustrating exemplary steps for providing enhanced structural visualization by temporal compounding of speckle tracked 3D ultrasound data for a moving object, in accordance with an embodiment of the invention. Referring to FIG. 3, there is shown a flow chart 300 comprising exemplary steps 302, 304, 306, 308, 310, 310a, 310b, and 310c.

In step 302, the ultrasound system 100 is operable to capture and record 3D ultrasound image data comprising a plurality of frames for an object as it moves.

In step 304, the ultrasound system 100 is operable to generate tracking information, for example, motion tracking and speckle tracking information, for a multitude of particular regions comprising the object based on the captured and recorded 3D ultrasound image data.

In step 306, the ultrasound system 100 is operable to reorganize and/or transform the 3D ultrasound image data so that pixels corresponding to the same tracked particular region of the object in each of the plurality of captured frames is grouped together, based on the generated tracking information.

In step 308, the ultrasound system 100 is operable to compound the plurality of captured frames in the image of the object by combining the pixels corresponding to the same tracked particular region of the object in each of the plurality of captured frames, which have been grouped together by, for example, averaging, median filtering, taking maximum and minimum values, etc.

In step 310, the ultrasound system 100 is operable to display resulting stationary single 3D frame of the tracked particular region of the object based on the compounded plurality of captured frames. In this regard, in one embodiment of the invention, in step 310a, the ultrasound system 100 is operable to cause display of the resulting stationary single 3D frame of the tracked particular region of the object by back transforming the single 3D stationary frame onto an original shape of the object. In another embodiment of the invention, in step 310b, the ultrasound system 100 is operable to display resulting stationary single 3D frame of the tracked particular region of the object as a map in relation to a stationary grid of the object. The single compounded stationary frame may also be transformed back onto all the different frames in a loop hence providing a dynamic view of the beating heart but without change in the structural delineation display except the morphing of it onto the different shapes of the heart throughout the loop. In step 310c, the ultrasound system 100 is operable to slice the corresponding dataset resulting from the compounding and render the tracked region of the object in 3D or utilize any 3D visualization to present a 3D image of the tracked region of the object.

In an exemplary embodiment of the invention, the ultrasound system 100 is operable to compound motion compensated ultrasound data from consistent regional locations of the heart through one or more heart cycles or any fraction thereof, for a feature or structure that may be fixed with respect to the walls of the heart. The ultrasound system 100 may be operable to enhance signal-to-noise ratio (SNR), fill out missing information and reduce reverberations and/or shadowing by combining information from varying insonification angles and allow structures to be visually comprehended.

Figure 4:
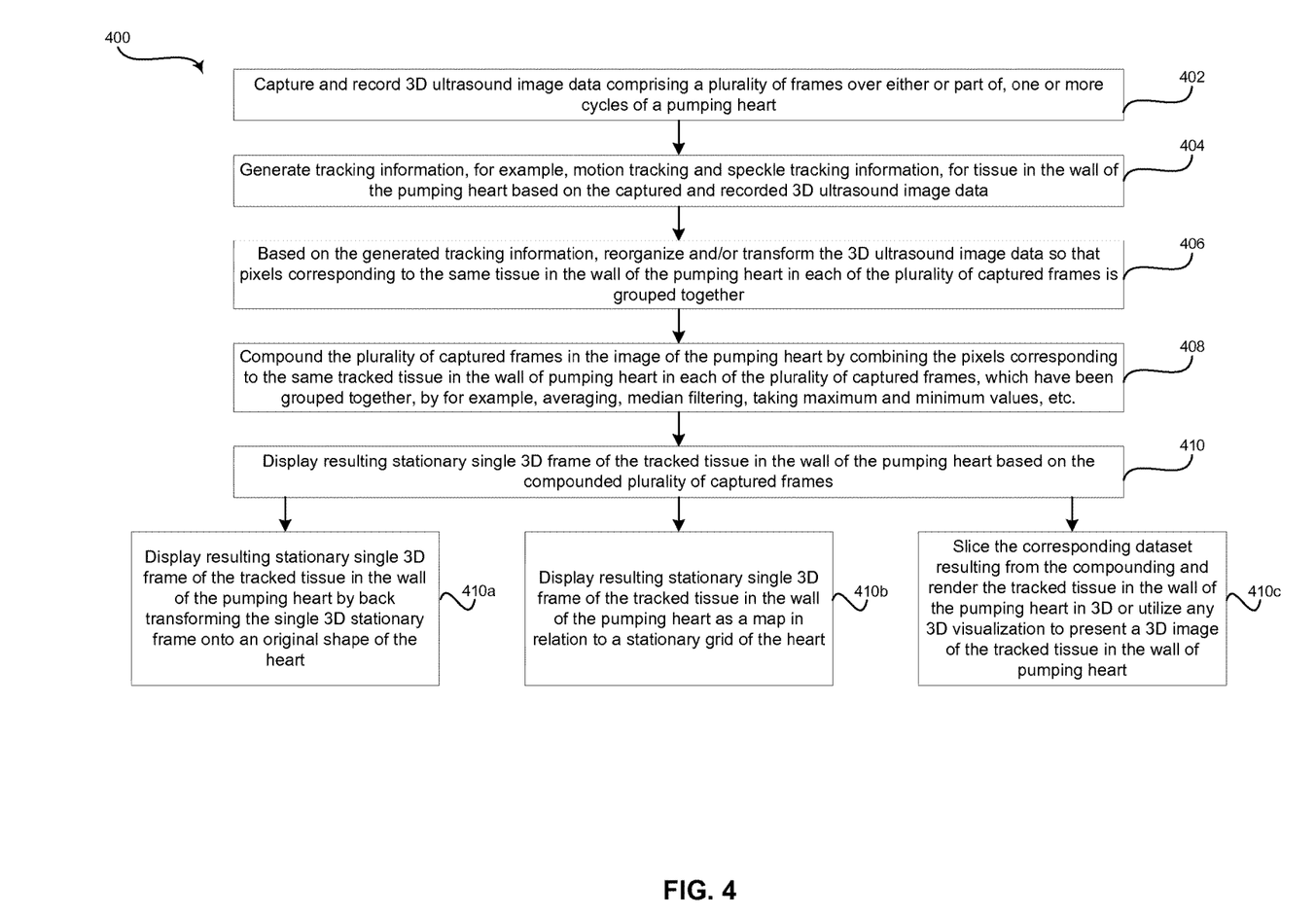
FIG. 4 is a flow chart illustrating exemplary steps for providing enhanced structural visualization by temporal compounding of speckle tracked 3D ultrasound data for a pumping heart, in accordance with an embodiment of the invention.

FIG. 4 is a flow chart illustrating exemplary steps for providing enhanced structural visualization by temporal compounding of speckle tracked 3D ultrasound data for a pumping heart, in accordance with an embodiment of the invention. Referring to FIG. 4, there is shown a flow chart 400 comprising exemplary steps 402, 404, 406, 408, 410, 410a, 410b, and 410c.

In step 402, the ultrasound system 100 is operable to capture and record 3D ultrasound image data comprising a plurality of frames over either a part of, one or more cycles of a pumping heart.

In step 404, the ultrasound system 100 is operable to generate tracking information, for example, motion tracking and speckle tracking information, for tissue in the wall of the pumping heart based on the captured and recorded 3D ultrasound image data.

In step 406, the ultrasound system 100 is operable to reorganize and/or transform the 3D ultrasound image data so that pixels corresponding to the same tissue in the wall of the pumping heart in each of the plurality of captured frames is grouped together, based on the generated tracking information.

In step 408, the ultrasound system 100 is operable to compound the plurality of captured frames in the image of the pumping heart by combining the pixels corresponding to the same tracked tissue in the wall of pumping heart in each of the plurality of captured frames, which have been grouped together, by for example, averaging, median filtering, taking maximum and minimum values, etc.

In step 410, the ultrasound system 100 is operable to display resulting stationary single 3D frame of the tracked tissue in the wall of the pumping heart based on the compounded plurality of captured frames. In step 410a, the ultrasound system 100 is operable to display resulting stationary single 3D frame of the tracked tissue in the wall of the pumping heart by back transforming the single 3D stationary frame onto an original shape of the heart. In step 410b, the ultrasound system 100 is operable to display resulting stationary single 3D frame of the tracked tissue in the wall of the pumping heart as a map in relation to a stationary grid of the heart. In step 410c, the ultrasound system 100 is operable to slice the corresponding dataset resulting from the compounding and render the tracked tissue in the wall of the pumping heart in 3D or utilize any 3D visualization to present a 3D image of the tracked tissue in the wall of pumping heart.

In accordance with an embodiment of the invention, an ultrasound device 100 may be operable to acquire ultrasound image data corresponding to a plurality of volume frames of an object and apply motion compensation to the acquired ultrasound image data to track different particular regions of the object. The ultrasound device 100 may be operable to compound the motion compensated ultrasound image data that corresponds to the tracked particular regions of the object within the plurality of volume frames of the object. The ultrasound device 100 may be operable to generate a stationary single three dimensional (3D) volume of the tracked particular regions of the object. The ultrasound device may be operable to acquire the ultrasound image data over at least a portion of a movement cycle that corresponds to the plurality of volume frames of the object. The ultrasound device may be operable to generate motion tracking information and speckle tracking information from the acquired ultrasound image data for the tracked particular regions of the object. The ultrasound device 100 may be operable to group pixels corresponding to each of the tracked particular region of the object based on the generated motion tracking information and speckle tracking information.

The ultrasound device 100 is operable to combine the grouped pixels corresponding to each of the tracked particular region of the object utilizing, for example, averaging, median filtering, and a maximum and minimum values. The ultrasound device 100 is operable to display the stationary single three dimensional (3D) volume of the tracked particular region of the object based on the combined grouping of the pixels corresponding to the tracked particular region of the object. The ultrasound device 100 may be operable to render a three dimensional (3D) visualization of the tracked particular region of the object based on sliced portions of the grouped pixels corresponding to the tracked particular region of the object.

In accordance with various embodiments of the invention, the enhanced structural visualization by temporal compounding of speckle tracked 3D ultrasound data as disclosed herein may be combined with contrast agents to further enhance imaging.

In another embodiment of the invention, a non-transitory computer readable medium having stored computer program comprises at least one code section that is executable by a machine for causing the machine to perform steps disclosed herein. Exemplary steps may comprise acquiring ultrasound image data corresponding to a plurality of volume frames of an object and applying motion compensation to the acquired ultrasound image data to track, or align between frames, a particular structure in the object within the plurality of volume frames of the object. The motion compensated ultrasound image data that corresponds to the tracked particular structure in the object within the plurality of volume frames of the object may be compounded and a stationary single three dimensional (3D) volume of the tracked particular structure in the object may be generated. At least a portion of the plurality of volume frames of the object may be replaced by the compounded static frame morphed back onto the shape of the heart in the particular phase of the heart cycle that volume comes from in order to be able to visually track the particular structure in the object. This morphing may be based on motion tracking information and/or speckle tracking information generated from the acquired ultrasound image data.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for enhanced structural visualization by temporal compounding of speckle tracked 3D ultrasound data.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
    acquiring ultrasound image data corresponding to a plurality of subsequent volume frames of an object;
    applying motion compensation to said acquired ultrasound image data to track, or align between frames, any particular region of said object within said plurality of volume frames of said object;
    compounding said motion compensated ultrasound image data that corresponds to said tracked particular region of said object within said plurality of volume frames of said object; and
    generating a stationary single three dimensional (3D) volume of a plurality of said tracked particular regions of said object.

2. The method according to claim 1, comprising acquiring said ultrasound image data over at least a portion of a movement cycle corresponding to said plurality of volume frames of said object.

3. The method according to claim 1, comprising generating motion tracking information from said acquired ultrasound image data for said tracked particular regions of said object.

4. The method according to claim 3, comprising generating speckle tracking information from said acquired ultrasound image data for said tracked particular regions of said object.

5. The method according to claim 4, comprising grouping pixels corresponding to each of said tracked particular region of said object based on said generated motion tracking information, and based on said generated speckle tracking information.

6. The method according to claim 5, comprising combining said grouped pixels corresponding to said each of said tracked particular region of said object.

7. The method according to claim 6, wherein said combining utilizes one or more of an averaging function, a median filtering function, and a maximum and minimum values function.

8. The method according to claim 6, comprising displaying said stationary single three dimensional (3D) volume of said tracked particular region of said object based on said combined grouping of said pixels corresponding to said tracked particular region of said object.

9. The method according to claim 6, comprising rendering a three dimensional (3D) visualization of said tracked particular region of said object based on sliced portions of said grouped pixels corresponding to said tracked particular region of said object.

10. A system, comprising:
    an ultrasound device, said ultrasound device be operable to:
        acquire ultrasound image data corresponding to a plurality of volume frames of an object;
        apply motion compensation to said acquired ultrasound image data to track, or align between frames, a particular region of said object within said plurality of volume frames of said object;
        compound said motion compensated ultrasound image data that corresponds to said tracked particular region of said object within said plurality of volume frames of said object; and generate a stationary single three dimensional (3D) volume of a plurality of said tracked particular regions of said object.

11. The system according to claim 10, wherein said ultrasound device is operable to acquire said ultrasound image data over at least a portion of a movement cycle corresponding to said plurality of volume frames of said object.

12. The system according to claim 10, wherein said ultrasound device is operable to generate motion tracking information from said acquired ultrasound image data for said tracked particular region of said object.

13. The system according to claim 12, wherein said ultrasound device is operable to generate speckle tracking information from said acquired ultrasound image data for said tracked particular region of said object.

14. The system according to claim 13, wherein said ultrasound device is operable to group pixels corresponding to each of said tracked particular region of said object based on said generated motion tracking information, and based on said generated speckle tracking information.

15. The system according to claim 14, wherein said ultrasound device is operable to combine said grouped pixels corresponding to said each of said tracked particular region of said object.

16. The system according to claim 15, wherein said combining utilizes one or more of an averaging function, a median filtering function, and a maximum and minimum values function.

17. The system according to claim 15, wherein said ultrasound device is operable to display said stationary single three dimensional (3D) volume of said tracked particular region of said object based on said combined grouping of said pixels corresponding to said tracked particular region of said object.

18. The system according to claim 15, wherein said ultrasound device is operable to render a three dimensional (3D) visualization of said tracked particular region of said object based on sliced portions of said grouped and compounded pixels corresponding to said tracked particular region of said object.

19. A non-transitory computer readable medium having stored thereon, a computer program having at least one code section, the at least one code section being executable by a machine for causing the machine to perform steps comprising:

acquiring ultrasound image data corresponding to a plurality of volume frames of an object;

applying motion compensation to said acquired ultrasound image data to track, or align between frames, a particular structure in said object within said plurality of volume frames of said object;

compounding said motion compensated ultrasound image data that corresponds to said tracked particular structure in said object within said plurality of volume frames of said object; and generating a stationary single three dimensional (3D) volume of said tracked particular structure in said object.

20. The non-transitory computer readable medium according to claim 19, comprising morphing at least a portion of said plurality of volume frames of said object to track said particular structure in said object, wherein said morphing is based on motion tracking information and speckle tracking information generated from said acquired ultrasound image data.

* * * * *